United States Patent
Ghose et al.

(10) Patent No.: US 10,909,462 B2
(45) Date of Patent: Feb. 2, 2021

(54) MULTI-DIMENSIONAL SENSOR DATA BASED HUMAN BEHAVIOUR DETERMINATION SYSTEM AND METHOD

(71) Applicant: Tata Consultancy Services Limited, Mumbai (IN)

(72) Inventors: Avik Ghose, Kolkata (IN); Arpan Pal, Kolkata (IN); Arindam Pal, Kolkata (IN); Tanushyam Chattopadhyay, Kolkata (IN); Santa Maiti, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 798 days.

(21) Appl. No.: 15/160,440

(22) Filed: May 20, 2016

(65) Prior Publication Data

US 2016/0342905 A1 Nov. 24, 2016

(30) Foreign Application Priority Data

May 21, 2015 (IN) .......................... 1998/MUM/2015

(51) Int. Cl.
*G06F 15/18* (2006.01)
*G06N 5/02* (2006.01)
(Continued)

(52) U.S. Cl.
CPC .............. *G06N 5/02* (2013.01); *G06N 5/022* (2013.01); *G06N 20/00* (2019.01); *G06Q 50/01* (2013.01)

(58) Field of Classification Search
CPC ....... G06N 3/00–126; G06N 5/00–048; G06N 7/00–08
(Continued)

(56) References Cited

U.S. PATENT DOCUMENTS 5,626,140 A * 5/1997 Feldman .............. G06K 9/6293
600/483
7,031,884 B1 * 4/2006 Radulovic ............... H04L 43/00
702/189
(Continued)

FOREIGN PATENT DOCUMENTS

WO WO 2008/030493 A2 3/2008

OTHER PUBLICATIONS

Vikram Chandrasekaran, "Measuring Vital Signs using Smart Phones", 2010, Master of Science Thesis, University of North Texas.*
(Continued)

*Primary Examiner* — Jue Louie
(74) *Attorney, Agent, or Firm* — Finnegan, Henderson, Farabow, Garrett & Dunner, LLP (57) ABSTRACT

A multi-dimensional sensor data analysis system and method is provided. The multi-dimensional sensor data analysis system receives indoor and outdoor location, online and physical activity, online and physical proximity and additional a plurality of inputs (specific to a user), for example, surrounding of the subject, physiological parameters of the subject and recent social status of the subject, both online and offline. The multi-dimensional sensor data analysis system processes these inputs along with the knowledge of past behavior and traditional parameters of location, proximity and activity by performing a multi-dimensional sensor data analysis fusion technique, producing one or more outputs, for example, predicting or determining a human behaviour to a given stimuli.

10 Claims, 5 Drawing Sheets

(51) Int. Cl.
*G06N 20/00* (2019.01)
*G06Q 50/00* (2012.01)
(58) Field of Classification Search
USPC .................................................... 706/12–62
See application file for complete search history.

(56) References Cited

U.S. PATENT DOCUMENTS

| | | | | |
|---|---|---|---|---|
| 9,849,387 | B1* | 12/2017 | Johnson | A63F 13/56 |
| 10,154,460 | B1* | 12/2018 | Miller | H04W 52/0254 |
| 2008/0288573 | A1 | 11/2008 | Bellotti et al. | |
| 2010/0261530 | A1* | 10/2010 | Thomas | A63F 13/42 |
| | | | | 463/36 |
| 2014/0121540 | A1* | 5/2014 | Raskin | A61B 5/6898 |
| | | | | 600/479 |
| 2014/0228649 | A1* | 8/2014 | Rayner | A61B 5/1118 |
| | | | | 600/301 |
| 2015/0029014 | A1* | 1/2015 | Bande Martínez | G08B 21/06 |
| | | | | 340/439 |
| 2015/0262474 | A1* | 9/2015 | Olczak | G08B 29/185 |
| | | | | 340/506 |
| 2015/0305675 | A1* | 10/2015 | Miller | A61B 5/0205 |
| | | | | 600/301 |
| 2016/0103996 | A1* | 4/2016 | Salajegheh | G06F 11/3024 |
| | | | | 726/25 |

OTHER PUBLICATIONS

Lara et al., "Continela: A human activity recognition system based on acceleration and vital sign data", 2012, Pervasive and Mobile Computing 8, pp. 717-729.*
Lara et al., "A survey on Human Activity Recognition using Wearable Sensors", 2013, IEEE Communications Surveys & Tutorials, vol. 15, No. 3.*
Wang et al. "A system of human vital signs monitoring and activity recognition based on body sensor network" 2014, Sensor Review.*
Count Bayesie, "Parameter Estimation—The PDF, CDF, and Quantile Function", Apr. 15, 2015, retrieved from: https://www.countbayesie.com/blog/2015/4/4/parameter-estimation-the-pdf-cdf-and-quantile-function.*
Mafrur et al., "Modeling and discovering human behavior from smartphone sensing life log data for identification purpose", Human-centric Computing and Information Sciences, SpringerOpen Journal, vol. 5, No. 31, pp. 1-18, (2015) http://download.springer.com/static/pdf/953/art%253A10.1186%252Fs13673-015-0049-7.pdf?originUrl=http%3A%2F%2Flink.springer.com%2Farticle%2F10.1186%2Fs13673-015-0049-7&token2=exp=1463129768~acl=%2Fstatic%2Fpdf%2F953%2Fart%25253A10.1186%25252Fs13673-015-0049-7.pdf%3ForiginUrl%3Dhttp%253A%252F%252Flink.springer.com%252Farticle%252F10.1186%252Fs13673-015-0049-7*~hmac=73b85ce10b78758748fa552786031dae3561853ec621ec8a984d8f4d63596428.

* cited by examiner

| SENSOR TYPE 202 | SENSOR DATA/FACT 204 | DESCRIPTION 206 |
|---|---|---|
| WIFI AND INERTIAL SENSORS | LOCATION | PYHSICAL LOCATION OF A USER, REQUIRED FOR COMPUTING OPTIMAL ROUTES |
| WELLNESS/FITNESS WEARABLE DEVICE | STRESS | STRESS LEVEL OF THE USER FOR ASSESSING THE PANIC LEVEL AND PULSE RATE |
| BLUETOOTH (OR NFC) | PROXIMITY | HOW CLOSE IS THE USER TO OTHER USERS IN A GROUP |

FIG. 2

| SENSOR TYPE 302 | SENSOR DATA/FACT 304 | DESCRIPTION 306 |
|---|---|---|
| GPS AND INERTIAL SENSORS | LOCATION | PYHSICAL LOCATION OF A VEHICLE, WHICH FORMS A BASE FOR SURROUNDING |
| WELLNESS/FITNESS WEARABLE DEVICE | STRESS | STRESS LEVEL, AND PULSE RATE OF A DRIVER DRIVING THE VEHICLE |
| INERTIAL SENSORS, MICROPHONE, SOFT SENSING, ETC. | SURROUNDING | WHAT IS TRAFFIC CONDITION, ROAD CONDITION, SOUND AND AIR POLLUTION LEVELS |

FIG. 3

| SENSOR TYPE 402 | SENSOR DATA/FACT 404 | DESCRIPTION 406 |
|---|---|---|
| WIFI AND INERTIAL SENSORS AND BEACONS IN INFRA | LOCATION | PYHSICAL LOCATION OF A USER, ACCURATE TO AISLE LEVEL |
| WEARABLE DEVICE | POINT OF DECISION MAKING | POINT WHERE THE USER (OR CUSTOMER) DECIDES TO GO FOR AN ALTERNATIVE |
| TEMPERATURE SENSORS, CROWD SOURCED INFO | SURROUNDING | AMBIENCE IN A RETAIL STORE (E.G., A SHOPPING MALL) |
| SOCIAL NETWORK ANALYSIS/WEB MINING | SOCIAL SIGNAL | WILLINGNESS TO BUY, DISCUSSION ABOUT PRODUCTS/ITEMS IN RECENT PAST |

MULTI-DIMENSIONAL SENSOR DATA BASED HUMAN BEHAVIOUR DETERMINATION SYSTEM AND METHOD

PRIORITY CLAIM

This U.S. patent application claims priority under 35 U.S.C. § 119 to: India Application No. 1998/MUM/2015, filed on May 21, 2015. The entire contents of the aforementioned application are incorporated herein by reference.

TECHNICAL FIELD

This disclosure relates generally to sensor data analysis, and more particularly to a system and a method for analysis of sensor data for determining human behaviour.

BACKGROUND

Human behaviour modeling is based on the fact that human behaviour is usually repetitive in nature, past behaviour of humans can be used to create individual as well as aggregate models. These models are further used to analyze and predict future behaviour of humans and response to a given stimuli. Traditional models have considered indoor and outdoor locations, online and physical activities, online and physical proximities as primary sensorial inputs to create predictive models. However, such models are not completely accurate due to "temporal variations" in human behaviour owing to external factors.

SUMMARY

Embodiments of the present disclosure present technological improvements as solutions to one or more of the above-mentioned technical problems recognized by the inventors in conventional systems. For example, in one aspect, a processor implemented method is provided. A processor implemented method, comprising: obtaining, using one or more hardware processors, one or more inputs from one or more sources, wherein the one or more inputs are specific to a user, wherein the one or more inputs correspond to at least one of one or more contexts associated with the user and one or more environmental conditions; analyzing, using the one or more hardware processors, the one or more inputs corresponding to at least one of the one or more contexts associated with the user and the one or more environmental conditions; assigning, using the one or more hardware processors, one or more weights to the one or more analyzed inputs based on the one or more sources to obtain one or more weighted analyzed inputs. In an embodiment, the one or more weights are assigned to the one or more analyzed inputs based on at least one of a current location of the user, and an event associated with the user. The method further comprises fusing, using the one or more hardware processors, the one or more weighted analyzed inputs to derive one or more vital signs of the user. In an embodiment, the one or more weighted analyzed inputs are prioritized for fusing to derive the one or more vital signs of the user based on at least one of a current location of the user, and an event associated with the user. In an embodiment, the one or more weights are assigned to the one or more analyzed inputs using one or more machine learning techniques. The method further comprises determining, using the one or more hardware processors, a behavior of the user based on the one or more vital signs of the user.

In an embodiment, the one or more sources comprises at least one of one or more location sensors, one or more proximity sensors, one or more social signals, one or more environmental sensors, and one or more physiological sensors. In an embodiment, the one or more social signals comprises one or more blog posts, one or more feeds, one or more statuses indicating expressions of the user on one or more social media.

In another aspect, a system is provided. The system comprising: a memory storing instructions; one or more communication interfaces; one or more hardware processors coupled to the memory using the one or more communication interfaces, wherein the one or more hardware processors are configured by the instructions to: obtain one or more inputs from one or more sources, wherein the one or more inputs are specific to a user, wherein the one or more inputs correspond to at least one of one or more contexts associated with the user and one or more environmental conditions, analyze the one or more inputs corresponding to at least one of the one or more contexts associated with the user and the one or more environmental conditions, assign one or more weights to the one or more analyzed inputs based on the one or more sources to obtain one or more weighted analyzed inputs. In an embodiment, the one or more weights are assigned to the one or more analyzed inputs based on at least one of a current location of the user, and an event associated with the user.

The hardware processor is further configured to fuse the one or more weighted analyzed inputs to derive one or more vital signs of the user. In an embodiment, the one or more weighted analyzed inputs are prioritized for fusing to derive the one or more vital signs of the user based on at least one of a current location of the user, and an event associated with the user. In an embodiment, the one or more weights are assigned to the one or more analyzed inputs using one or more machine learning techniques. The hardware processor is further configured to determine a behavior of the user based on the one or more vital signs of the user.

In an embodiment, the one or more sources comprises at least one of one or more location sensors, one or more proximity sensors, one or more social signals, one or more environmental sensors, and one or more physiological sensors. In an embodiment, the one or more social signals comprises one or more blog posts, one or more feeds, one or more statuses indicating expressions of the user on one or more social media.

In yet another aspect, one or more non-transitory machine readable information storage mediums comprising one or more instructions are provided. The one or more instructions which when executed by one or more hardware processors causes obtaining one or more inputs from one or more sources, wherein the one or more inputs are specific to a user, wherein the one or more inputs correspond to at least one of one or more contexts associated with the user and one or more environmental conditions; analyzing the one or more inputs corresponding to at least one of the one or more contexts associated with the user and the one more environmental conditions; assigning one or more weights to the one or more analyzed inputs based on the one or more sources to obtain one or more weighted analyzed inputs. In an embodiment, the one or more weights are assigned to the one or more analyzed inputs based on at least one of a current location of the user, and an event associated with the user. The one or more instructions which when executed by one or more hardware processors further causes fusing the one or more weighted analyzed inputs to derive one or more vital signs of the user. In an embodiment, the one or more weighted analyzed inputs are prioritized for fusing to derive the one or more vital signs of the user based on at least one of a current location of the user, and an event associated with the user. In an embodiment, the one or more weights are assigned to the one or more analyzed inputs using one or more machine learning techniques. The one or more instructions which when executed by one or more hardware processors further causes determining, using the one or more hardware processors, a behavior of the user based on the one or more vital signs of the user.

In an embodiment, the one or more sources comprises at least one of one or more location sensors, one or more proximity sensors, one or more social signals, one or more environmental sensors, and one or more physiological sensors. In an embodiment, the one or more social signals comprises one or more blog posts, one or more feeds, one or more statuses indicating expressions of the user on one or more social media.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through 5, where similar reference characters denote corresponding features consistently throughout the figures, there are shown preferred embodiments and these embodiments are described in the context of the following exemplary system and/or method.

Figure 1:
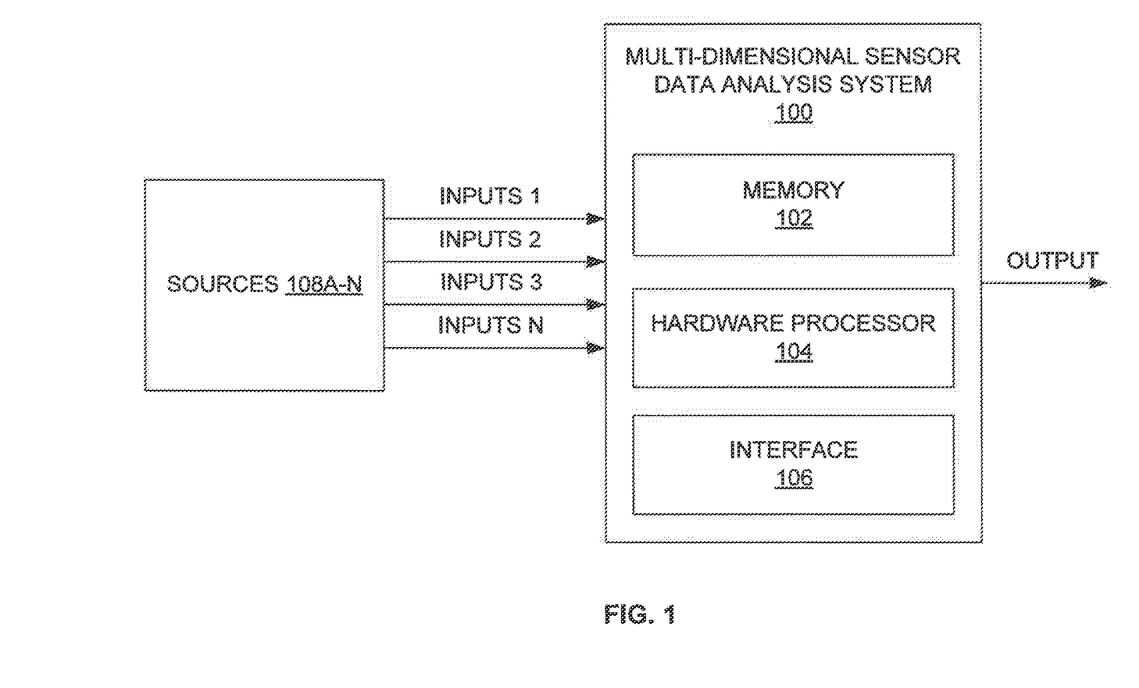
FIG. 1 illustrates a multi-dimensional sensor data analysis system according to an embodiment of the present disclosure.

FIG. 1 illustrates a multi-dimensional sensor data analysis system 100 according to an embodiment of the present disclosure. The multi-dimensional sensor data analysis system 100 (also referred hereinafter as the system 100) comprises a memory storing instructions 102, and a hardware processor 104 configured by the instructions to receive a plurality of inputs 1-N from one or more sources 106A-N and perform one or more methodologies described herein. The multi-dimensional sensor data analysis system 100 further comprises an interface 106. Although the exemplary block diagram and the associated description refers to a memory, a hardware processor, an I/O interface, it may be understood that one or more memory units, one or more hardware processors, and one or more I/O interfaces may be comprised in the system 100. The memory 102 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, a compact disks (CDs), digital versatile disc or digital video disc (DVDs) and magnetic tapes. The memory 102 further comprises module(s) (not shown in FIG. 1) to perform the methodologies described herein.

The multi-dimensional sensor data analysis system 100 is also referred as "sensor extrapolator". The multi-dimensional sensor data analysis system 100 may be implemented as any of a variety of conventional computing devices, including, for example, servers, a desktop PC, a notebook or portable computer, a workstation, a mainframe computer, an entertainment device, cellular phones, smart phones, personal digital assistants (PDAs), portable computers, desktop computers, tablet computers, phablets, and an internet appliance. The memory 102 may comprise knowledge of past anthropological behaviour corresponding to a particular user (or users), and the plurality of inputs 1-N received from the one or more sources 108A-N through a network.

The network may be a wireless network, a wired network, or a combination thereof. The network can also be an individual network or a collection of many such individual networks, interconnected with each other and functioning as a single large network, e.g., the Internet or an intranet. The network can be implemented as one of the different types of networks, such as intranet, local area network (LAN), wide area network (WAN), the internet, near field communication (NFC), and such. The network may either be a dedicated network or a shared network, which represents an association of the different types of networks that use a variety of protocols. Further, the network may include network devices, such as network switches, hubs, routers, HBAs, for providing a communication link between the multi-dimensional sensor data analysis system 100 and the one or more sources 108A-N.

The interface 106 (also referred as I/O interface) may include a variety of software and hardware interfaces, for example, a web interface, a graphical user interface, and the like. The I/O interface 106 may allow the system 100 to interact with a user directly or through the user devices. Further, the I/O interface 106 may enable the system 100 to communicate with other computing devices, such as web servers and external data servers (not shown). The I/O interface 106 can facilitate multiple communications within a wide variety of networks and protocol types, including wired networks, for example, LAN, cable, etc., and wireless networks, such as WLAN, cellular, or satellite. The I/O interface 106 may include one or more ports for connecting a number of devices to one another or to another server.

The plurality of inputs 1-N that are received from the one or more sources 108A-N, comprise, but are not limited to, location activity, physiological parameters, social signals (e.g., one or more feeds/statuses), and environmental sensing parameters. The one or more sources 108A-N comprises, but are not limited to, one or more computer systems, a mobile communication device, a wearable device, a third party device, a third party service provider, or combinations thereof, etc. For instance, the wearable device, or the communication device comprises one or more sensors, for example, physiological sensors, to record or capture one or more parameters, for example, electrocardiogram test results (also referred as EKG or ECG readings), Galvanic Skin Response (GSR), photoplethysmography (PPG), heat-flux. Based on these parameters, one or more vital signs associated with the user may be derived. Vital signs comprises, but are not limited to, body temperature, blood pressure, pulse (heart rate), and breathing rate (respiratory rate), or stress level, etc. Similarly, the wearable device, or the communication device comprises one or more sensors. The one or more sensors may execute, or otherwise are in communication with one or more applications hosted on the wearable device, or the communication device (or a third party device). The one or more sensors or the one or more applications are configured to capture or, otherwise are in communication with a social media to obtain, social signals such as an online activity or a physical activity. For example, an online activity comprises one or more blog posts, feeds, and/or statuses indicating expressions of the user. Physical activity comprises socializing within a community (e.g. in a friends circle or with colleagues), etc. The social signals are processed and analyzed to identify an ongoing activity (or ongoing activities) or a past activity (or past activities). Other sources comprise, but are not limited to, environmental sensors that involve both hard sensing in the infrastructure and soft sensing, for example, weather information, an event information, etc. The parameters when used by the multi-dimensional sensor data analysis system 100 (or by a behaviour modeling executed on the multi-dimensional sensor data analysis system 100) affect user behaviour and/or change in user behaviour in response to a given stimuli. For instance, A→B, B→C, then A→C. For example, "people are in a good mood when weather is sunny" and "people tend to shop when they are happy" implies that "there is higher chance of sale conversion when the weather is sunny." The output of such enhanced behaviour models can be used for enhancements in personalization and response planning.

The model implements "weighted mean" technique to implement the fusion technique. The fusion technique enables the system 100 to process the plurality of inputs 1-N to a given stimuli, and produce one or more outputs. The one or more outputs comprise of an expected response associated with the user. For a multi-sensor fusion, the weights are computed as an inverse of a probability distribution of each dimension over a given use-case, in one example embodiment. For example for certain cases, physiological parameters may provide accurate markers than social network analysis. In such a scenario, a plurality of physiological parameters may be prioritized over the social signals that are analysed. In other cases, environment sensor data may be prioritized over other sensor data. The weights are computed in accordance with the weighted mean equation below:

$$f = \frac{\sum_{i=1}^{n} w_i d_i}{\sum_{i=1}^{n} w_i}.$$

Where 'f' signifies the weight mean, $d_i$ signifies an ith dimension and $w_i$ signifies a weight for the ith dimension, and 'n' being a real number. Assuming an emergency evacuation plan, where the person's location, activity, proximity and stress levels are obtained. The prediction model is based on the measurement of the location, activity, proximity and stress levels. However, it may be observed that panic plays the most major role in a decision making, followed by "herd behavior". Hence the weight of a sensor (e.g., PPG) that indicates panic and a sensor that provides proximity (e.g., Bluetooth) may be higher than those that provide the location and activity (e.g., accelerometer and WiFi). In such a scenario, the fusion technique is implemented at a dimension level rather than at a sensor level. The model 'm' may be represented in accordance with the following expression:

$m$=[($W$proximity*$M$proximity+$W$panic*$M$panic+$W$location*$M$location)/($W$proximity+$W$panic+$W$location)].

'W' represents the weight assigned to the context (or analysed input obtained from a source), whereas 'M' represents measurement associated with the context (or analysed input obtained from a source). The weights are learned during controlled experiments scenarios that replicate an actual use-case closely and then the same weights may be applied. The weights are learned using one or more machine learning techniques, a set of labeled stimulus and corresponding recorded responses. This learning helps the system 100 to accurately assign in assigning weights, analyzing contexts from inputs, resulting in appropriate fusing, thereby leading to derive one or more vital signs that enable to more accurately determine user behavior based on the one or more vital signs.

When sensor data from different sensors are not available for different dimensions, indirect markers to the same may be available, through other, seemingly uncorrelated sensors and sources. This is achieved by performing controlled experiments of similar psychological conditions and observe the data from multiple sensors. For example, an excitement causes high heartrate which in turn is manifested as redness of face". Hence, in the absence of a pulse sensor, the same parameter (or a weight) may be derived by performing a multi-dimensional fusion may be performed based on importance score and confidence score. For certain given scenarios, the multi-dimensional sensor data analysis system 100 estimates a reading of a non-existent sensor required for the use-case using the sensors that exist in the environment, based on previously unknown correlations by scenario design and controlled experimentation.

As described above, the multi-dimensional sensor data analysis system 100 may implement the modules to perform the above methodologies. For example, the multi-dimensional sensor data analysis system 100 comprises a multi-dimensional fusion module that when executed by the hardware processor 104, fuses the mentioned paradigms of location, proximity, activity, social signals, physiology and environmental factors to obtain a better prediction (or near-accurate) of a person's response, given a stimuli and a condition. The multi-dimensional sensor data analysis system 100 further comprises a modeling module when executed by the hardware processor 104, captures user's response given a condition and stimuli n a controlled environment, and retrieves an appropriate model from a set of models (stored in the memory 102) for given a real-life condition and predict the user behavior based on past models. The multi-dimensional sensor data analysis system 100 further comprises a sensor extrapolation module when executed by the hardware processor 104, captures correlation between seemingly uncorrelated sensors rather than correlated sensors (e.g., health and motion sensors are related because running may cause increase in heart-rate). The uncorrelated sensors comprises, for example, an image capture device such as a camera and a heart-rate sensor. Thus, when somebody is in panic, it is reflected both in an increased heart-rate and also facial expression/redness, and this is used for correlation in similar conditions to recreate the estimated values from missing sensors using available sensors to feed the fusion module. The estimated values from above example can be, when a person's facial expression is 'X', though no direct measurement of panic is possible, the panic level can be estimated using other sensors or sensor data. The multi-dimensional fusion module, the modeling module, the sensor extrapolation module are implemented as a logically self-contained part of a software program that when executed perform the above method described herein, in one embodiment. The multi-dimensional fusion module, the modeling module, the sensor extrapolation module are implemented as a self-contained hardware component, in another embodiment. The multi-dimensional fusion module, a modeling module, a sensor extrapolation module may be implemented as a self-contained hardware component, with a logically self-contained part of a software program embedded into each of the hardware component.

Figure 2:
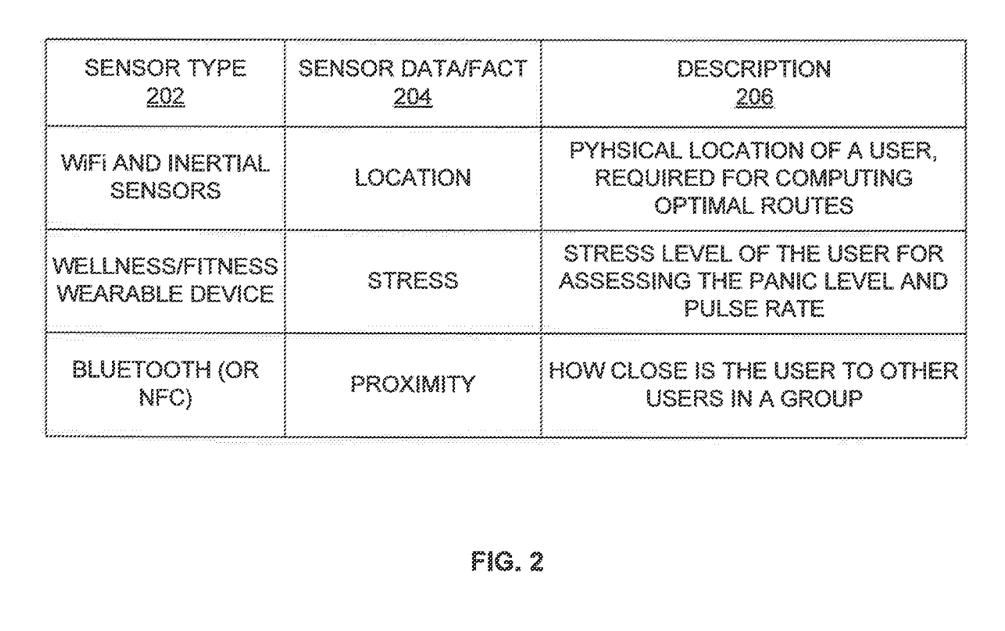
FIG. 2 illustrates an exemplary table view of sensor data captured during a first event, according to an embodiment of the present disclosure.

FIG. 2, with reference to FIG. 1, illustrates an exemplary table view of sensor data captured during a first event, according to an embodiment of the present disclosure. In particular, FIG. 2 depicts a table view illustrating a sensing map during an emergency evacuation. One or more instructions are provided to one or more trapped subjects (e.g., or users) according to an optimal plan based on occupancy and transition capacities of various exits and associated corridors. In such a scenario when the above instructions are sent, there is no guarantee that the users follow the instructions. Thus, the optimal plan accounts the probability of a user following the instruction given his/her current context and the scenario. Typically, location is used for planning. The multi-dimensional sensor data analysis system 100 uses received proximity sensor data and physiology parameters. For example, proximity to a crowd moving towards a particular exit may incite the user to follow. Further, current pulse rate of the user may indicate that his/her level of panic shall affect the human's decision making capability accordingly. The user may behave in the same manner as people of similar persona do during a panic. This behavior information can be used to re-plan ahead of time, which may lead to better evacuation time and saving of more human lives during such emergency evacuation.

As depicted in the table, the table view includes a sensor type field 202, a sensor data field 204, and a description field 206. The sensor type field 202 comprises one or more sources, for examples, sensors that capture sensor data during an emergency. The sensors comprise, but are not limited to, a WiFi and inertial sensors, a physiological sensor such as a stress sensor, and a proximity sensor. The sensor data field 204 comprises sensor data pertaining to the sensors and the users. For instance, the WiFi and inertial sensors may capture a physical location of the user, for computing optimal routes. The location information may also be required for design of probabilistic behaviour models, in one example embodiment. Similarly, wellness/fitness wearable devices may capture sensor data such as the pulse rate which is indicative of the stress. The stress level of the user enables the multi-dimensional sensor data analysis system 100 to assess level of panic. Similarly, NFC (Near field communication) components on a wearable device (or a mobile communication device), for example, a Bluetooth (or NFC) on the user's mobile communication device, captures proximity data which is indicative of how close is the user to other users in a group (to determine the behaviour of the user, and as well as the other users in the group). This proximity data enables the multidimensional sensor data analysis system 100 to determine the group of users and their behaviour.

Figure 3:
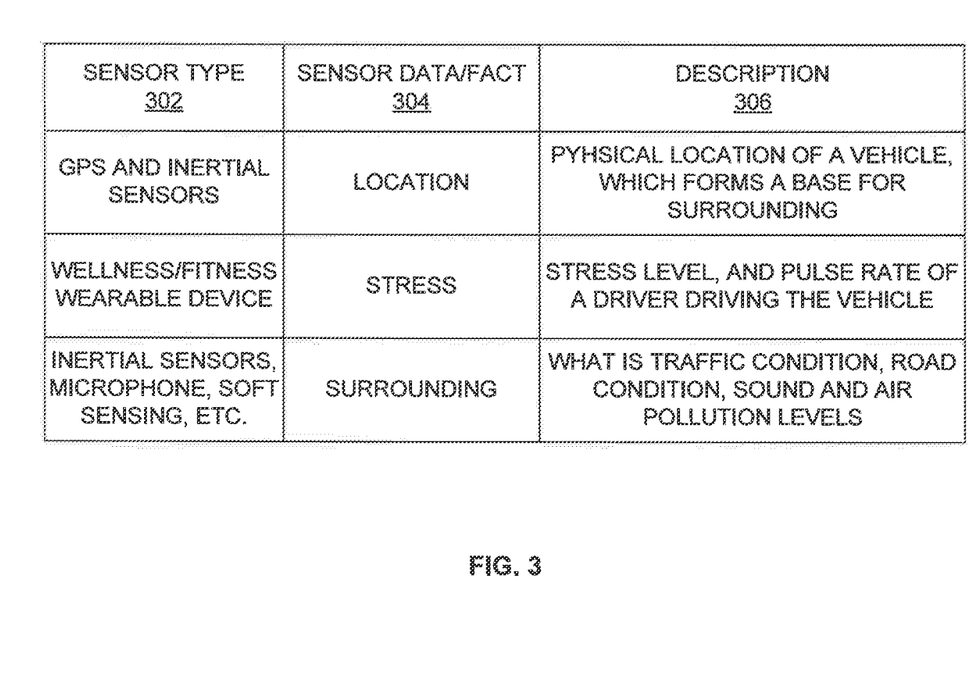
FIG. 3 illustrates an exemplary table view of sensor data captured during a second event according to an embodiment of the present disclosure.

FIG. 3, with reference to FIGS. 1 through 2, illustrates an exemplary table view of sensor data captured during a second event according to an embodiment of the present disclosure. In particular, FIG. 3 depicts a table view illustrating a sensing map during driving. Assuming a person driving a vehicle. The driver's response to a given event during a drive (e.g., a trip) depends on the road condition, the vehicle condition, the driver's usual behavior, for example, aggressive, cautious etc., the surroundings, for example, traffic and sound/air pollution level, and the driver's current state.

As depicted in the table, the table view includes a sensor type field 302, a sensor data field 304, and a description field 306. The sensor type field 302 comprises one or more sources, for examples, sensors that capture sensor data while driving the vehicle. The sensors comprise, but are not limited to, a Global Positioning System (GPS) and inertial sensors, a physiological sensor such as a stress sensor, a phone inertial sensor, mobile device microphone, soft sensing device, infrastructure sensing device, crowd sensing (congestion), and anemometer. The sensor data field 304 comprises sensor data pertaining to the sensors and the users. For instance, the GPS and inertial sensors may capture a physical location of the vehicle which forms a base for the surrounding. Similarly, wellness/fitness wearable devices may capture sensor data such as the pulse rate which is indicative of the stress level of the driver. The stress level of the user enables the multi-dimensional sensor data analysis system 100 to assess level of panic. Similarly, the phone inertial sensor, the mobile device microphone, the soft sensing device, the infrastructure sensing device, the crowd sensing (congestion), and the anemometer may capture the surrounding data, for example, traffic condition, road condition, sound pollution levels, air pollution level, etc.

Figure 4:
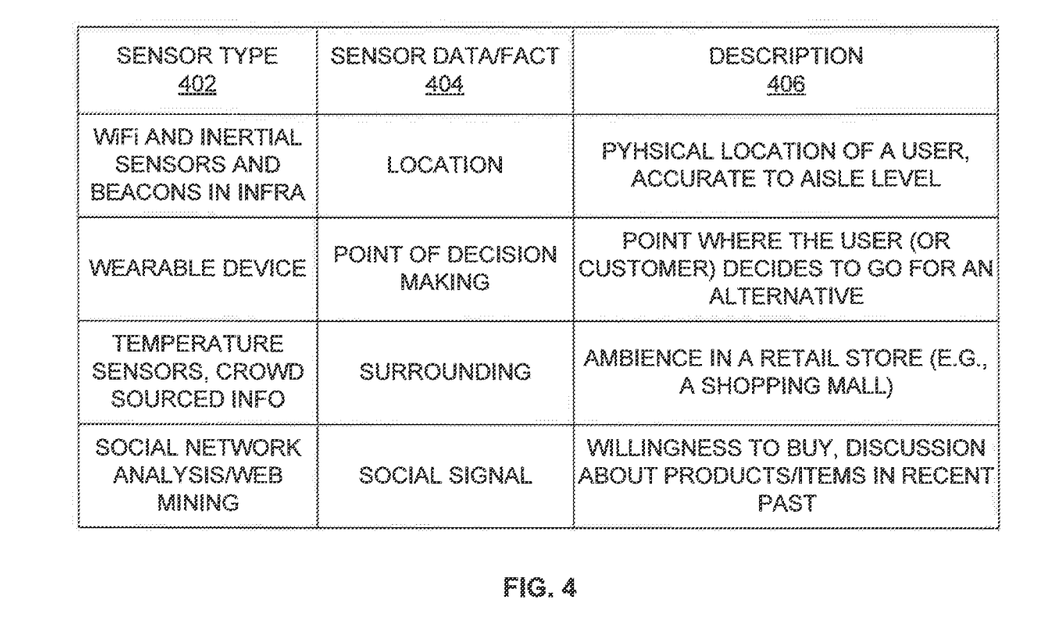
FIG. 4 illustrates an exemplary table view of sensor data captured during a third event according to an embodiment of the present disclosure.

FIG. 4, with reference to FIGS. 1 through 3, illustrates an exemplary table view of sensor data captured during a third event according to an embodiment of the present disclosure. In particular, FIG. 4 depicts a table view illustrating a sensing map during a consumer in a retail store. Unlike, traditional system and method which use only location and duration as input, the multi-dimensional sensor data analysis system uses the point of decision./indecision sensor data as important as other data for pushing an incentive to make a sell. The physiological parameters may provide hints into such moments for a consumer.

As depicted in the table, the table view includes a sensor type field 402, a sensor data field 404, and a description field 406. The sensor type field 402 comprises one or more sources, for examples, sensors that capture sensor data while driving the vehicle. The sensors comprise, but are not limited to, WiFi and inertial sensors on user's mobile communication device and beacons in the infrastructure of the retail store, wearable devices or wearable sensors, temperature sensors, humidity sensor, crowd-sourced information, and social media (or social network analysis, web mining), etc. The sensor data field 304 comprises sensor data pertaining to the sensors and the users. For instance, the WiFi and inertial sensors on user's mobile communication device and beacons in the infrastructure of the retail store may capture a physical location of a person, accurate to aisle level. Similarly, wearable devices or wearable sensors may capture sensor data such as the pulse rate, GSR, heat-flux, pupil scan, etc., which is indicative of the point of decision making. Similarly, the temperature sensors, the humidity sensor, crowd-sourced information may capture an ambience in the retail store (e.g., a shopping mall) or surrounding. Similarly, the social media (or social network analysis, web mining), etc., capture social signals such as emoticons, expression or statuses, that are indicative of willingness to buy, discussion of products/items in recent past.

Figure 5:
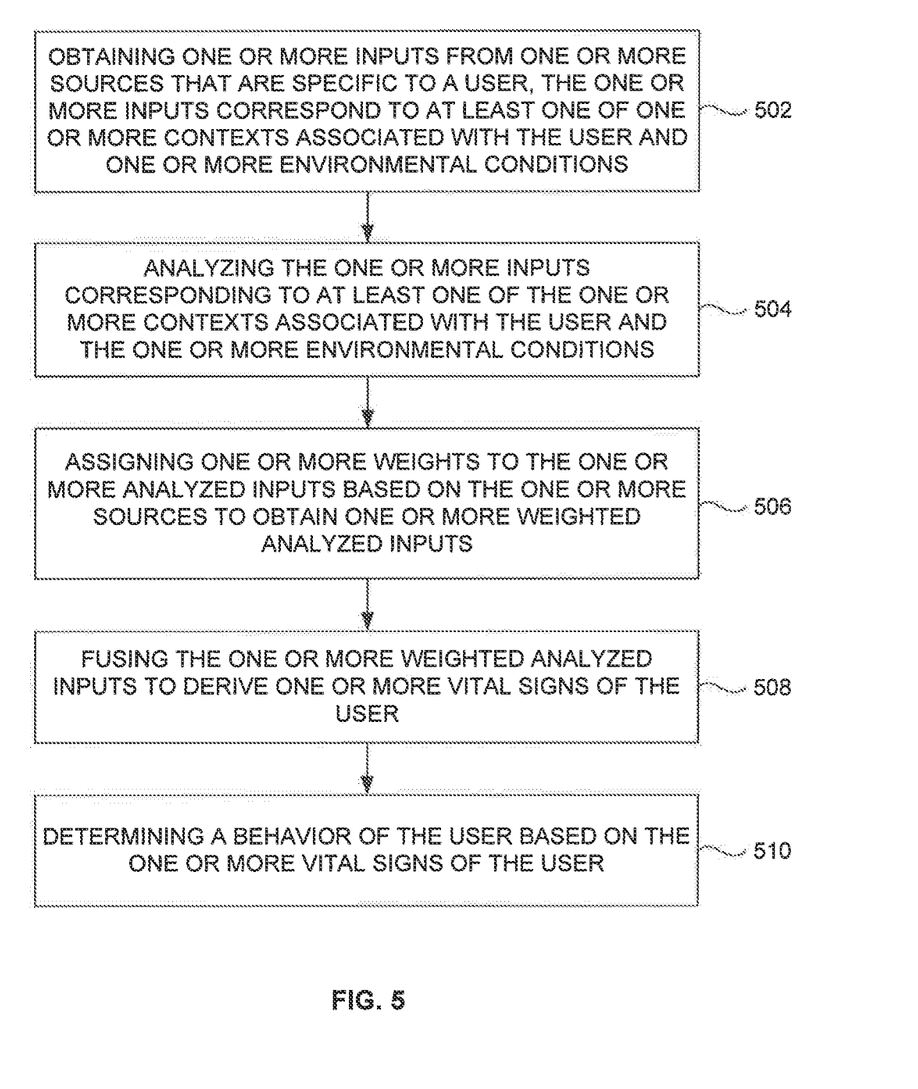
FIG. 5 is a flow diagram illustrating a processor implemented method for determining behavior of a user using the multi-dimensional sensor data analysis system of FIG. 1 according to an embodiment of the present disclosure.

FIG. 5, with reference to FIGS. 1 through 4, is a flow diagram illustrating a processor implemented method for determining behavior of a user using the multi-dimensional sensor data analysis system 100 of FIG. 1 according to an embodiment of the present disclosure. The steps of the method of the present disclosure will now be explained with reference to the components of the system 100 as depicted in FIG. 1. The hardware processor 104 is configured by the instructions stored in the memory 102. The hardware processor 104 when configured by the instructions determines behavior of one or more users as described hereinafter. In an embodiment, at step 502, the hardware processor 104 obtaining one or more inputs from the one or more sources 108A-N, wherein the one or more inputs are specific to a user, wherein the one or more inputs correspond to at least one of one or more contexts associated with the user and one or ore environmental conditions. In an embodiment, the one or more sources 108A-N comprises but are not limited to, at least one of one or more location sensors, one or more proximity sensors, one or more social signals, one or more environmental sensors, one or more physiological sensors, and the like. In another embodiment, the one or more social signals comprises, but are not limited to, one or more blog posts, one or more feeds, one or more statuses indicating expressions of the user on one or more social media, and the like. At step 504, the hardware processor 104, analyzes said one or more inputs corresponding to at least one of the one or more contexts associated with the user and the one or more environmental conditions. More particularly, at this step, the hardware processor 104 analyses the contexts associated with the user, including the environmental conditions (e.g., obtained from one or more environmental sensors).

At step 506, the hardware processor 104 assigns one or more weights to the one or more analyzed inputs based on the one or more sources 108A-N to obtain one or more weighted analyzed inputs. More specifically, the hardware processor 104 assigns weight to the one or more contexts associated with the user. In an embodiment, the hardware processor 104 assigns the one or more weights to the one or more analyzed inputs (e.g., the one or more contexts) based on at least one of a current location of the user (e.g., a building), and an event associated with the user (e.g., the user being involved in an evacuation plan during an emergency). At step 508, the hardware processor 104 fuses the one or more weighted analyzed inputs (e.g., the one or more weighted contexts) to derive one or more vital signs of the user. At step 510, the hardware processor 104 determines a behavior (or behaviours) of the user based on the one or more vital signs of the user. In a scenario such as emergency evacuation and the like, one or more weighted analyzed inputs (e.g., the weighted contexts) are prioritized over other inputs (received from other sources amongst the sources 106A-N) for fusing to derive the one or more vital signs of the user based on at least one of a current location of the user, and an event associated with the user. In an embodiment, the one or more weights are assigned to the one or more analyzed inputs (or the one or more contexts or the one or more analysed contexts) using one or more machine learning techniques.

Unlike, conventional systems and methods which utilize indoor and outdoor location, online and physical activity, online and physical proximity as primary sensorial inputs, the multi-dimensional sensor data analysis system 100 receives indoor and outdoor location, online and physical activity, online and physical proximity and additional a plurality of inputs (specific to a user), for example surrounding of the subject, physiological parameters of the subject and recent social status of the subject, both online and offline. The multi-dimensional sensor data analysis system 100 processes these plurality of inputs along with the knowledge of past behavior and traditional parameters of location, proximity and activity by performing a multi-dimensional sensor data analysis fusion technique (e.g., using one or more fusion techniques), thereby improving an accuracy of one or more outputs for example, predicting or determining a human behaviour to a given stimuli. Further, the multi-dimensional sensor data analysis system 100 learns the weights for fusion in a given scenario using one or more machine learning techniques. The output(s) produced by the multi-dimensional sensor data analysis system 100 may be provided to one or more service providers who can utilize (or implement) in their corresponding systems, and offer/cater one or more tailored services (including one or more products). Controlled experiments are performed by the multi-dimensional sensor data analysis system 100, and outputs from seemingly uncorrelated sensors are recorded to identify correlations using techniques of cross correlation discovery. Causal analysis is done to physically verify the correlation, in the absence of a critical (or an important) sensor. Other sensors (not critical) can be used to extrapolate the values based on previously learned correlation. The multi-dimensional sensor data analysis system 100 accounts for the effects of surrounding, social signal, user context and physiological parameters to predict human behavior. The multi-dimensional sensor data analysis system 100 further models user behavior in controlled experiments and then use the same models to predict user behavior in the wild. This enables to extrapolate missing sensors based on context and perform multi-sensor correlation based on the same.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
obtaining, using one or more hardware processors, one or more inputs from one or more sensors, wherein said one or more inputs are specific to a user, wherein said one or more inputs correspond to at least one context from amongst one or more contexts associated with said user and one or more environmental conditions associated with the said user, wherein the one or more sensors comprises a critical sensor and other sensors;
analyzing, using said one or more hardware processors, said at least one context from amongst one or more contexts and said one or more environmental conditions;
assigning, using said one or more hardware processors, one or more weights to the analyzed at least one context from amongst one or more contexts based on said one or more sensors to obtain one or more weighted analyzed inputs;
performing a multi-sensor fusing, using said one or more hardware processors, on said one or more weighted analyzed inputs, wherein the assigned one or more weights are computed in an inverse of a probability distribution of each dimension over a use-case and using a weighted mean technique to derive one or more vital signs of said user based on at least one of a current location of the user, and an event associated with the user, wherein the fusion is based on prioritization of the at least one context from amongst one or more contexts, wherein the computed one or more weights are learned during controlled experiment scenarios replicating the use-case, and wherein the computed one or more weights are learned using one or more machine learning techniques, a set of labeled stimulus and corresponding recorded responses, and wherein the derived one or more vital signs enable determining user behavior of the at least one of the context from amongst one or more contexts; and
identifying, using said one or more hardware processors, correlation between the critical sensor and the other sensors to extrapolate a missing sensor using uncorrelated sensors, wherein the missing sensor is used for further fusing at least one context from amongst one or more contexts.

2. The processor implemented method of claim 1, wherein said one or more sensors comprises at least one of one or more location sensors, one or more proximity sensors, one or more social signals, one or more environmental sensors, and one or more physiological sensors.

3. The processor implemented method of claim 2, wherein said one or more social signals comprises one or more blog posts, one or more feeds, one or more statuses indicating expressions of said user on one or more social media.

4. A system comprising:
a memory storing instructions;
one or more communication interfaces;
one or more hardware processors coupled to said memory using said one or more communication interfaces, wherein said one or more hardware processors are configured by said instructions to:
obtain one or more inputs from one or more sensors, wherein said one or more inputs are specific to a user, wherein said one or more inputs correspond to at least one context from amongst one or more contexts associated with said user and one or more environmental conditions associated with the said user, wherein the one or more sensors comprises a critical sensor and other sensors, analyze said at least one of context from amongst one or more contexts and said one or more environmental conditions, assign one or more weights to the analyzed at least one context from amongst one or more contexts based on said one or more sensors to obtain one or more weighted analyzed inputs, perform a multi-sensor fusing on said one or more weighted analyzed inputs, wherein the assigned one or more weights are computed in an inverse of a probability distribution of each dimension over a use-case and using a weighted mean technique to derive one or more vital signs of said user based on at least one of a current location of the user, and an event associated with the user, wherein the fusion is based on prioritization of at least one context from amongst one or more contexts, wherein the computed one or more weights are learned during controlled experiment scenarios replicating the use-case, and wherein the computed one or more weights are learned using one or more machine learning techniques, a set of labeled stimulus and corresponding recorded responses, and wherein the derived one or more vital signs enable determining user behavior of the at least one of the context from amongst one or more contexts; and identify correlation between the critical sensor and the other sensors to extrapolate a missing sensor using uncorrelated sensors, wherein the missing sensor is used for further fusing at least one context from amongst one or more contexts.

5. The system of claim 4, wherein said one or more sensors comprises at least one of one or more location sensors, one or more proximity sensors, one or more social signals, one or more environmental sensors, and one or more physiological sensors.

6. The system of claim 5, wherein said one or more social signals comprises one or more blog posts, one or more feeds, one or more statuses indicating expressions of said user on one or more social media.

7. The system of claim 4, wherein said one or more weights are assigned to said one or more analyzed inputs using one or more machine learning techniques.

8. One or more non-transitory machine readable information storage mediums comprising one or more instructions which when executed by one or more hardware processors causes:

obtaining, using one or more hardware processors, one or more inputs from one or more sensors, wherein said one or more inputs are specific to a user, wherein said one or more inputs correspond to at least one context from amongst one or more contexts associated with said user and one or more environmental conditions associated with the said user, wherein the one or more sensors comprises a critical sensor and other sensors;

analyzing, using said one or more hardware processors, said at least one context from amongst one or more contexts and said one or more environmental conditions;

assigning, using said one or more hardware processors, one or more weights to said at least one context from amongst one or more contexts based on said one or more sensors to obtain one or more weighted analyzed inputs;

performing a multi-sensor fusing, using said one or more hardware processors, on said one or more weighted analyzed inputs, wherein the assigned one or more weights are computed in an inverse of a probability distribution of each dimension over a use-case and using a weighted mean technique to derive one or more vital signs of said user based on at least one of a current location of the user, and an event associated with the user, wherein the fusion is based on prioritization of the at least one context from amongst one or more contexts, wherein the computed one or more weights are learned during controlled experiment scenarios replicating the use-case, and wherein the computed one or more weights are learned using one or more machine learning techniques, a set of labeled stimulus and corresponding recorded responses, and wherein the derived one or more vital signs enable determining user behavior of the at least one of the context from amongst one or more contexts; and identifying, using said one or more hardware processors, correlation between the critical sensor and the other sensors to extrapolate a missing sensor using uncorrelated sensors, wherein the missing sensor is used for further fusing at least one context from amongst one or more contexts.

9. The one or more non-transitory machine readable information storage mediums of claim 8, wherein said one or more sensors comprises at least one of one or more location sensors, one or more proximity sensors, one or more social signals, one or more environmental sensors, and one or more physiological sensors.

10. The one or more non-transitory machine readable information storage mediums of claim 9, wherein said one or more social signals comprises one or more blog posts, one or more feeds, one or more statuses indicating expressions of said user on one or more social media.

* * * * *